(12) United States Patent
Het Lam et al.

(10) Patent No.: US 11,197,732 B2
(45) Date of Patent: Dec. 14, 2021

(54) DEVICE FOR SUSPENDING ONE OR MORE MEDICAL INSTRUMENTS, SUCH AS A DRYING CABINET FOR ENDOSCOPES AND HOLDING SYSTEM FOR SUSPENDING ONE OR MORE MEDICAL INSTRUMENTS

(71) Applicant: Wassenburg Medical B.V., Dodewaard (NL)

(72) Inventors: Jan Willem Het Lam, Dodewaard (NL); Edwin Petrus Elisabeth Van Opstal, Dodewaard (NL); Maurits Sybrandus Augustinus De Koning, Dodewaard (NL); Jan Roelof Abel Kortstra, Dodewaard (NL)

(73) Assignee: Wassenburg Medical B.V.

( * ) Notice: Subject to any disclaimer, the term of this patent is extended or adjusted under 35 U.S.C. 154(b) by 606 days.

(21) Appl. No.: 16/082,980

(22) PCT Filed: Mar. 7, 2017

(86) PCT No.: PCT/EP2017/055337
§ 371 (c)(1),
(2) Date: Sep. 7, 2018

(87) PCT Pub. No.: WO2017/153414
PCT Pub. Date: Sep. 14, 2017

(65) Prior Publication Data
US 2019/0090973 A1    Mar. 28, 2019

(30) Foreign Application Priority Data

Mar. 7, 2016  (NL) ...................................... 2016373

(51) Int. Cl.
*A61B 1/00*  (2006.01)
*A61B 50/20*  (2016.01)
(Continued)

(52) U.S. Cl.
CPC .......... *A61B 50/20* (2016.02); *A61B 1/00144* (2013.01); *A61B 1/121* (2013.01); *A61B 50/10* (2016.02); *A61B 2050/105* (2016.02)

(58) Field of Classification Search
CPC ..... A61B 50/10; A61B 50/20; A61B 1/00144; A61B 1/121; A61B 2050/105
See application file for complete search history.

(56) References Cited

U.S. PATENT DOCUMENTS 468,224 A    2/1892  Kennedy, Jr.
4,711,352 A * 12/1987  Williams ........... B65D 73/0007
                                                206/363
(Continued)

FOREIGN PATENT DOCUMENTS

JP    2010119514    6/2010

OTHER PUBLICATIONS

International Search Report and Written Opinion for corresponding PCT App. No. PCT/EP2017/055337 dated Aug. 4, 2017.

*Primary Examiner* — Timothy J Neal
*Assistant Examiner* — William B Chou
(74) *Attorney, Agent, or Firm* — Emerson, Thomson & Bennett, LLC; Roger D. Emerson; Peter R. Detorre (57) ABSTRACT

The present invention relates to a device for suspending one or more medical instruments, such as a drying cabinet for endoscopes, comprising a closable space, a plurality of holders positioned in the closable space provided with at least one retaining elements and a control system comprising an identification system configured for identifying the holders, wherein the at least one retaining element of each holder is provided with at least one identification means connected to the identification system, wherein the identification means is configured to identify the retaining element of the respective holder. The present invention further relates to a holding system for suspending one or more medical instruments in (Continued)

a closable space adapted therefore, such as a drying cabinet for endoscopes, comprising a holder and at least one retaining element, wherein the holding system further comprises a spacer connected to the holder and provided with a hinge system, wherein the at least one retaining element is configured to clampingly receiving the at least one medical instrument to be suspended.

20 Claims, 5 Drawing Sheets

(51) Int. Cl.
*A61B 50/10* (2016.01)
*A61B 1/12* (2006.01)

(56) References Cited

U.S. PATENT DOCUMENTS

| | | | |
|---|---|---|---|
| 2002/0146344 A1* | 10/2002 | Walta | A61B 50/10 422/28 |
| 2008/0314789 A1 | 12/2008 | Thomas | |
| 2010/0191049 A1 | 7/2010 | Mandava | |
| 2015/0077249 A1 | 3/2015 | Rahim | |
| 2015/0154434 A1 | 6/2015 | Rahim | |

* cited by examiner

DEVICE FOR SUSPENDING ONE OR MORE MEDICAL INSTRUMENTS, SUCH AS A DRYING CABINET FOR ENDOSCOPES AND HOLDING SYSTEM FOR SUSPENDING ONE OR MORE MEDICAL INSTRUMENTS

The present invention relates to a device for suspending one or more medical instruments, such as a drying cabinet for endoscopes. The present invention further relates to a holding system for suspending one or more medical instruments in a closable space adapted therefore, such as a drying cabinet for endoscopes.

Devices for suspending medical instruments, such as a drying cabinet for endoscopes, are well known. Such devices are configured to suspend medical instruments wherein the medical instruments are suspended in the device by human interaction, i.e. by an operator involved in the process of washing and drying medical instruments, such as endoscopes. Due to the lengthy flexible part of, for example, endoscopes, the holders for holding the endoscopes to be suspended are located at a predefined height to prevent contact of the distal end of the flexible part of an endoscope with the base of the device the endoscope is suspended in.

Unfortunately, the height of the holders for suspending the medical instruments is chosen such that the operator has to work over his head, i.e. connecting the medical instrument to be suspended to the device. Consequently, the devices for suspending medical instruments available on the market nowadays are not ergonomically designed.

Further, it is of utmost importance that the operator is able to connect the identified medical instrument to be suspended with the correct available holder identified by the device. Several identification systems have been described in the prior art, however, the identification systems described have shortcomings with regard to reproducibility of the safety of the system.

To overcome the above-identified shortcomings of the devices currently available, the present invention provides hereto a device for suspending one or more medical instruments, such as a drying cabinet for endoscopes, comprising a closable space for receiving one or more medical instruments to be suspended, a plurality of holders positioned in the closable space, wherein each of the holders is configured to hold one or more medical instruments, and wherein each of the holders is provided with at least one retaining element for holding a medical instrument to be suspended and a control system comprising an identification system configured for identifying the holders. In order to improve the reproducibility of the safety of the device according to the present invention, the at least one retaining element of each holder is provided with at least one identification means connected to the identification system, wherein the identification means is configured to identify the retaining element of the respective holder. By providing identification means which are able to identify the retaining element of a respective holder, the incorrect connection of a medical instrument to be suspended is reduced to the absolute minimum. Where the identification systems described in the prior art provide identification of the respective holders, the present invention further identifies the specific retaining elements the medical instrument is actually connected to, once received by the respective holder. By identifying the retaining element instead of the holder a retaining element is connected with, the operator is able to identify the correct position the medical instrument to be suspended has to be connected with.

Preferably, the at least on retaining element is configured to retain the control body of a medical instrument to be suspended to the holder. By providing a retaining element configured to retain the control body coupling of the control body to the holder is facilitated in an easy and reproducible way. In order to improve the reproducibility and safety of the coupling of a medical instrument, e.g. the control body of an endoscope, to the device of the present invention, the retaining element may comprise a bracket. The bracket may be configured to clampingly or releasably receiving a medical instrument to be suspended.

In a preferred embodiment of the present invention, the at least one retaining element comprises a ring-shaped passage opening for receiving the control body of the medical instrument to be suspended. The control body of the medical instrument may be slid into the passage opening. Due to the fact that the control body of the medical instrument to be suspended is typically connected to another, more lengthy, flexible part of the medical instrument, the peripheral wall of the ring-shaped passage opening is provided with an opening for receiving such other part of the medical instrument connected to the control body, such as the flexible part of an endoscope.

The identification means of the present invention may include various types of identification means. Preferably, the at least one identification means comprises a visual identification means for identifying by means of visual indication the retaining element of the respective holder. The visual indication of the retaining element of the respective holder may be provided by a light source, such as one or more LED lamps. Preferably, the light source comprises different coloured LED lamps not only to identify each of the retaining elements, but also to provide further information to the operator about, for example, the availability or status of the retaining element the LED lamps are connected to.

Further, the light source may be arranged on or in the holder and positioned such that the light source illuminates the retaining element. By illuminating the retaining element, the operator is perfectly able to identify the respective retaining element based on one visual observation. In a preferred embodiment, the light source may be arranged on the position the retaining element is connected to the respective holder. By providing the light source on that specific position, the retaining element can be most efficiently illuminated.

In order to further improve the efficiency of illuminating the retaining element, the retaining element is preferably made from a light-guiding material, such as an illuminating material. The retaining element may comprise a semi-transparent plastic, such as polypropylene.

In a further embodiment of the present invention, the plurality of holders is displaceable relative to each other. By providing a device wherein each of the holders can be displaced individually, the operator is able to access a specific holder without the need of displacing all holders at the same time. Further, the operator is able to access a specific holder without running the risk of accidentally replace one holder by the other holder and, consequently, connect the medical instrument to the incorrect holder.

Any displacement of a holder will potentially lead to an increased risk of the incorrect coupling of a medical instrument to be suspended to a respective holder. To avoid any problems with regard to the displacement of the holder, the at least one identification means is preferably positioned such that by displacement of the holder, the position of the identification means relative to the retaining element is unchanged. The correct identification of the respective retaining element, and thus the correct coupling of a medical device with the respective retaining element and holder connected to the retaining element, is herewith safeguarded by the device according to the present invention.

The device according to the present invention may comprise a drying cabinet for drying endoscopes. Inherently, the one or more medical instruments to be suspended may comprise an endoscope. Typically, the closable space of the drying cabinet for drying endoscopes comprises a drying space.

The control system of the device of the present invention may further comprise a status indication system for displaying the status of a medical instrument connected with a holder. In a preferred embodiment, the status indication system is connected to the at least one identification means for displaying the status of the medical instrument connected with the respective holder. By providing the status indication system wherein the status is incorporated into the identification means, the operator is able to monitor the status of the medical instrument connected with the holder by simply consult the identification means correlated to the respective endoscope.

Alternatively, the device of the present invention may comprise at least one status indication means in addition to, or instead of, the at least one identification means. In case the device comprises at least one status indication means instead of the at least one identification means as defined above, the at least one retaining element of each holder is provided with at least one status indication means connected to the status indication system of the control system. In such embodiment, each of the holders of the device of the present invention, and in particular the at least one retaining element, is able to display the status of the medical instrument connected with the respective holder. Since the status indication means are directly related to a specific retaining element, it has to be understood that the status indication means may serve as identification means as well.

In case use is made of visual identification means, the operator is able to visually monitor the status of a medical instrument suspended in the closable space. For example, in case the device includes a drying cabinet for endoscopes, the operator is able to monitor the individual drying process of each of the endoscopes. Once the drying process of an endoscope is completed, the operator is able to remove the endoscope from the device without consulting any display situated next to the door of the closable space. Thus, increasing the efficiency and correct removal of each of the endoscopes from the device.

In order to increase the ergonomically design of a device according to the present invention, the present invention further relates to a holding system for suspending one or more medical instruments in a closable space adapted therefore, such as a drying cabinet for endoscopes, comprising a holder for holding at least one medical instrument and at least one retaining element connected to the holder for retaining at least one medical instrument to the holder, wherein the holding system further comprises a spacer with a first end connected to the holder and a second end provided with a hinge system for hingedly connecting the spacer to a back wall of the closable space. The holding system thus provides the possibility of moving the holder downward in a direction facing away from a back wall the hinge system might be connected to, in order to lower the height of the holder and to provide easy access of the holder by the operator. By providing a holding system wherein the holder is moved downward in a direction facing away from a back wall the hinge system might be connected to, the relative orientation of the medical instrument retained by the holder with respect to the operator is changed. The holding system thus provides a more ergonomically design of a device for suspending medical instruments.

It is emphasized that the relative orientation change of the medical instrument results in a significantly more ergonomically design. For example, in the drying process for endoscopes, the endoscope is provided with a plurality of inlets to be connected to the drying cabinet to dry the internal channels of the endoscope, i.e. to flush the internal channels of the endoscopes with air. Typically the inlets to be connected to the drying cabinet are situated on the top part of the endoscope facing the top part of the drying cabinet once the endoscope is suspended in the drying cabinet. By changing the relative orientation of the endoscope to the operator, i.e. changing the relative orientation of the endoscope from the orientation in suspension to the orientation the endoscope is connected and disconnected to the retaining element of the holder system, the operator is able to easily access the plurality of inlets to be connected to the drying cabinet. In fact, the plurality of inlets are visual by the operator, further minimizing any incorrect arrangement of the connections to be made by the operator.

Preferably, the at least one retaining element is configured to clampingly receiving the at least one medical instrument to be suspended. By moving the holder of the holding system up and down, any medical instrument connected to the holder might drop from the holder during movement of the holder. Therefore, the holder according to the present invention comprises retaining elements whereby the medical instrument connected to the holder is releasably fixed to the respective holder. In a further preferred embodiment, the retaining element is configures to retain a control body of the medical instrument to be suspended to the holder.

The clampingly retaining of the medical instrument by the retaining element may be provided by providing at least one retaining element comprising a ring-shaped passage opening for receiving the control body of the medical instrument to be suspended. The peripheral wall of the ring-shaped passage opening may further be provided with an opening for receiving another part of the medical instrument connected to the control body, such as the flexible part of an endoscope.

The hinge system of the holding system according to the present invention may be configured to damp a downward movement of the holder in a direction facing away from the back wall, to avoid any accidental release of the medical instrument connected to the respective holder once the lowest point of the holder is reached. Also, the hinge system may be configured to automatically move the holder from a predefined position of the holder in an upward direction toward the back wall, to facilitate further ergonomically movement of the holder.

The holding system according to the present invention is preferably provided with two or more retaining elements, e.g. two pairs of retaining elements, for receiving not more than two medical instruments. Such holding system is able to receive on both sides of the first end of the spacer one medical instrument to be suspended.

In order to facilitate the correct suspension of the suspending part of the medical instrument, typically the lengthy, flexible part of an endoscope, the spacer is preferably provided with one or more guiding elements for guiding along the guiding elements the respective suspending part of the medical instrument received by the holder. Preferably, the spacer is provided with four guiding elements to sufficiently guide the suspending part along the spacer and to optimize such guidance in relation to the length of the spacer.

In a preferred embodiment, the guiding elements are positioned on the spacer according to a zigzag-pattern. The guiding elements are positioned such that the bending radius of the flexible suspended part of the medical instrument received by the holder is not smaller than 4 centimetre, to avoid damage of the suspending part of the medical instrument. It is noted that in order to provide a holding system wherein various types of medical instruments may be received, the guiding elements are positioned such that the bending radius of the flexible suspended part is not smaller than 6 centimetre. In order to provide a holding system suitable for all kind of medical instruments, the guiding elements are positioned such that the bending radius is not smaller than 8 centimetre.

In order to provide a holding system comprising a spacer arranged thereon the guiding elements described above suitable for suspending various types of medical instruments, such as endoscopes having a great variety in diameter of the flexible part, the guiding elements are positioned such that a zigzag-pattern is formed by the guiding elements wherein the angle of the vertices is within the range of 45° to 65°. Preferably, the angle of the vertices is within the range of 50° to 60°. Most medical instruments may be suspended in case the guiding elements are positioned such that a zigzag-pattern is formed by the guiding elements wherein the angle of the vertices is about 55°.

The spacer of the holding system according to the present invention may have any suitable length. In order to provide a holding system suitable for devices for suspending medical devices, the distance between the first end and the second end of the spacer is within the range of 50 centimetre to 90 centimetre, preferably the distance is within the range of 60 to 80 centimetre, even more preferably the distance between the first end and the second end of the spacer is about 70 centimetre.

In order to increase the operator's accessibility to the control body of a medical instrument connected to the retaining element of the holder system according to the present invention, the at least one retaining element is configured such that the angle between the spacer and the control body of a medical instrument to be suspended received by the at least one retaining element is within the range of 30° to 80°, preferably within the range of 50° to 70°. The most optimum access to the control body is provided by an angle of about 60°.

The present invention further relates to a device for suspending one or more medical instruments, such as a drying cabinet for endoscopes, comprising the device described above, wherein each of the plurality of holders positioned in the space comprises the holding system according to the present invention. In such system the second end of the spacer is preferably hingedly connected to the back wall of the closable space.

In order to provide an even further ergonomically design, the second end of the spacer is connected to the back wall of the closable space at a height within the range of 90 centimetre to 170 centimetre, preferably the second end is connected at a height within the range of 110 centimetre to 150 centimetre, more preferably at a height of about 125 centimetre.

The operator's accessibility to the holder and retaining elements of the holding system of the present invention is further depending on the angle of movement of the spacer of the holding system. Preferably, the hinge system is configured such that the angle between the spacer and the back wall of the closable space does not exceed 90°, preferably does not exceed 85°, more preferably does not exceed 80°.

In order to provide the optimal position of a medical instrument once suspended into the device, the hinged system may be configured such that the angle between the spacer and the back wall of the closable space is at least 0°, preferably at least 4°, more preferably at least 8°. Further the at least one retaining element of each of the holder may be configured such that the angle between the back wall of the closable space and a control body of a medical instrument suspended in the closable space received by the at least one retaining element is within the range of 40° to 70°, preferably within the range of 50° to 60°, more preferably about 55°. In such embodiment, the control body is located in the device such that optimal processing of the control body is possible.

In order to avoid any interference between adjacent medical instruments suspended in the device, the hinge systems of the plurality of holder positioned in the closable space are preferably connected to the back wall according to a wavy pattern.

In the following, the present invention will be explained further based on the accompanying drawings, which show the following.

Figure 1A:
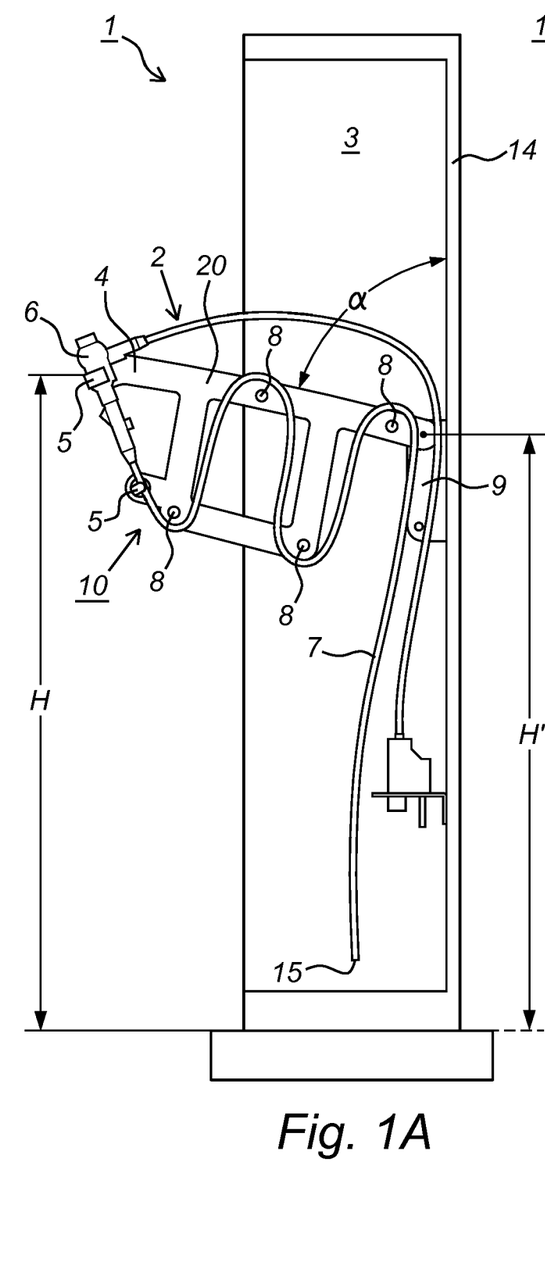
FIG. 1A-B: a schematic representation (side view) of the device according to the present invention.
Figure 1B:
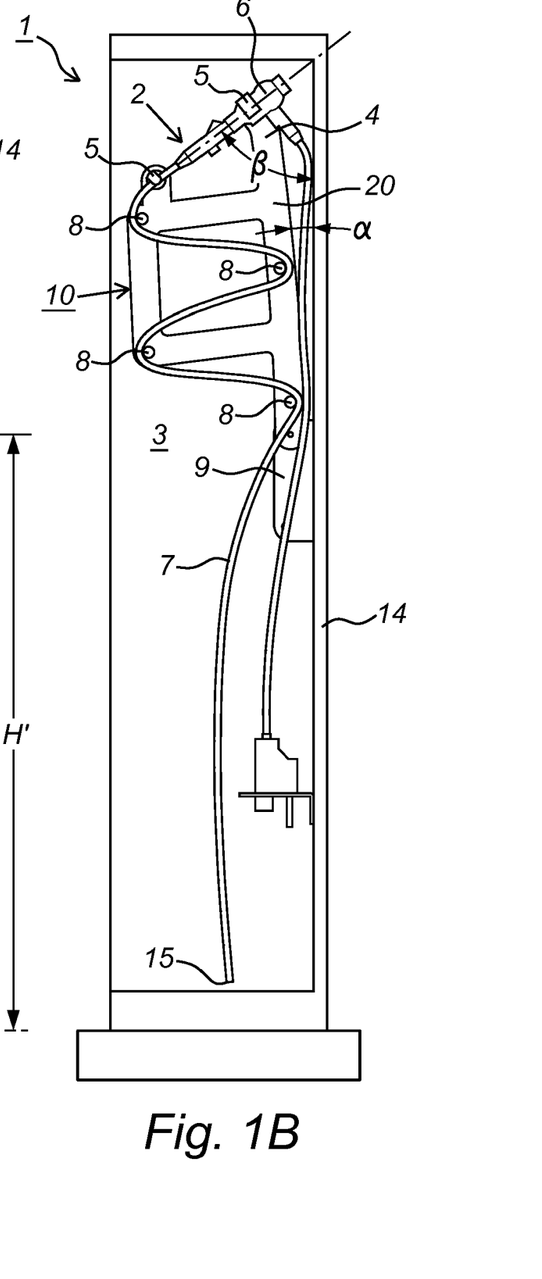

FIGS. 1A and 1B shows a schematic representative (side view) of the device 1 of the present invention. The device 1 comprises a space 3 typically closed by using a door (not shown). The device 1 is provided with a holding system 10 comprising a spacer 20 hingedly connected to the back wall 14 via hinge system 9. The spacer 20 is further provided with holder 4 comprising retaining elements 5. The retaining elements 5 are configured to retain or releasable hold the control body 6 of a medical instrument 2, such as an endoscope. The spacer 20 is further provided with guiding elements 8 for guiding the flexible part 7 of the medical instrument 2 along the spacer 20.

In FIG. 1A, the holding system 10 is positioned such that the holder 4 is easily accessible to the operator (not shown). The operator is able to easily retain the control body 6 of the medical instrument 2 to the holder 4 using the retaining elements 5. Preferably, the access height H of the holder 4 correlates to the average body length of the operators involved in the process of the disinfection and drying of medical instruments 2. By guiding the flexible part 7 of the medical instrument 2 along the guiding elements 8, the distal end 15 of the flexible part 7 is still suspended in the closable space 3 in the upward position (FIG. 1B) of the holding system 10 as well as the downward position of the holding system 10 shown in FIG. 1A.

The height H' of the connection of the spacer 20 with the back wall 14 depends on the maximum allowed angle α of the spacer 20 to the back wall 14. In case the angle α is 90°, the height H' corresponds to the access height H. Preferably, the angle α is about 72°. The access height H is preferably about 140 centimetres.

FIG. 1B shows the holding system 10 being in upward position. The retaining elements 5 of the holder 4 of holding system 10 are positioned such that the control body 6 of the medical instrument 2 retained in the retaining elements 5 at an angle β to the back wall 14. Preferably angle β is about 55°. Further it is noted that the angle α is preferably as small as possible. The angle α is preferably about 8°. Again it is noted that the distal end 15 of the flexible part 7 of the medical instrument 2 is still suspended in the closable space 3.

Figure 2:
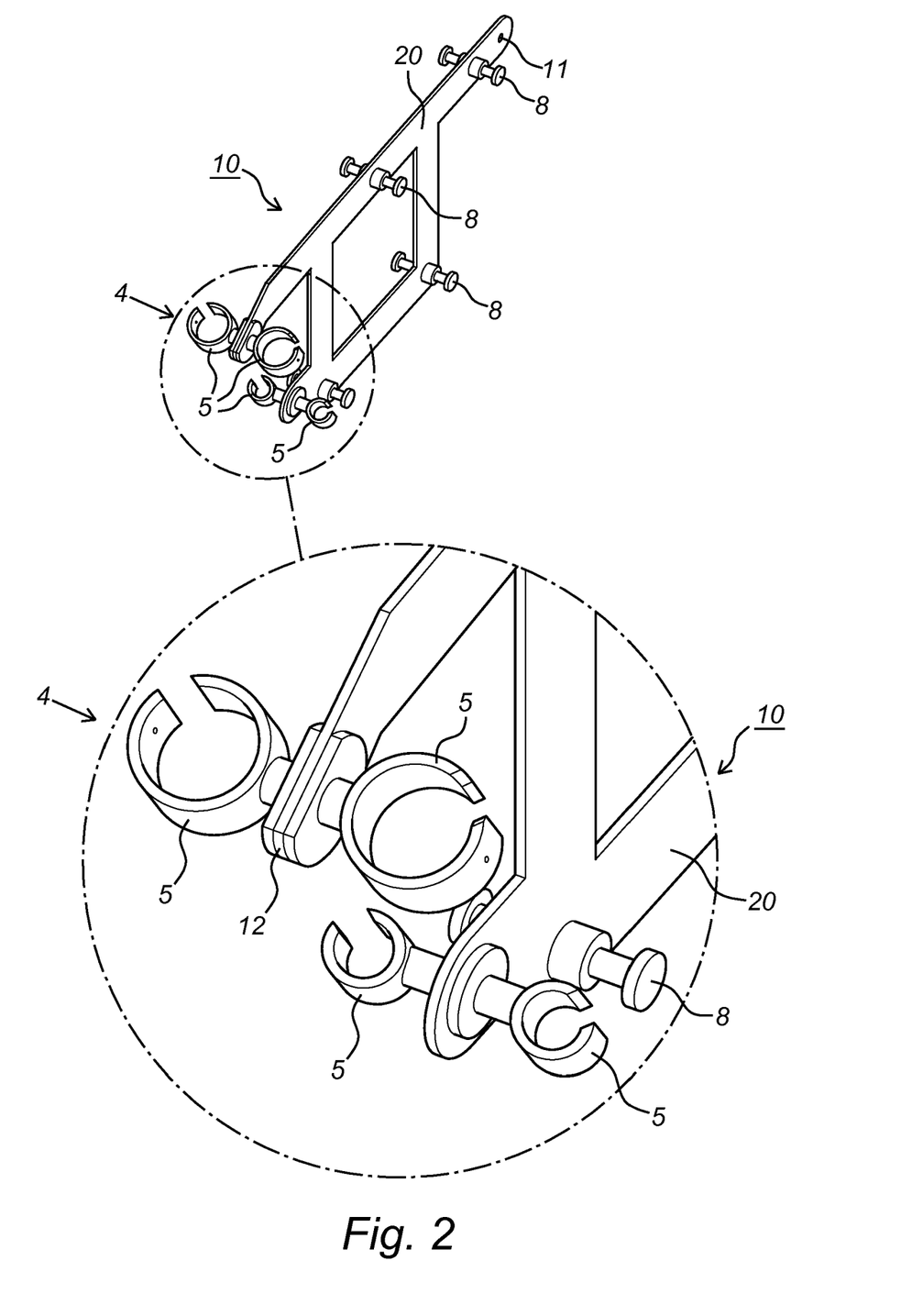
FIG. 2: a perspective view and detailed view of the holding system according to the present invention.

FIG. 2 shows a perspective view and detailed view of the holding system according to the present invention. FIG. 2 shows that perspective view of the spacer 20 comprising several guiding elements 8 and a holder 4 comprising several retaining elements 5. In the detailed view, it is shown that the retaining elements 5 comprises a annular or ring-shaped passage opening, wherein an opening is provided in the peripheral wall for receiving at least the flexible part 7 of the medical instrument 2. Once the flexible part 7 is received by the retaining elements 5, the control body 6 of the medical instrument 2 is slipped into the retaining elements 5 for releasably fixing the medical instrument 2 to the holder 4 of the holding system 10.

The spacer further comprises a first end 12 for connecting the holder 4 to the spacer 20. The spacer further comprises a second end 11 for connecting the spacer 20 to the device 1 of the present invention. Preferably, the first end 12 is provided with identification means, such as a LED-light, for identifying the retaining element 5 the identification means is connected with.

Figure 3:
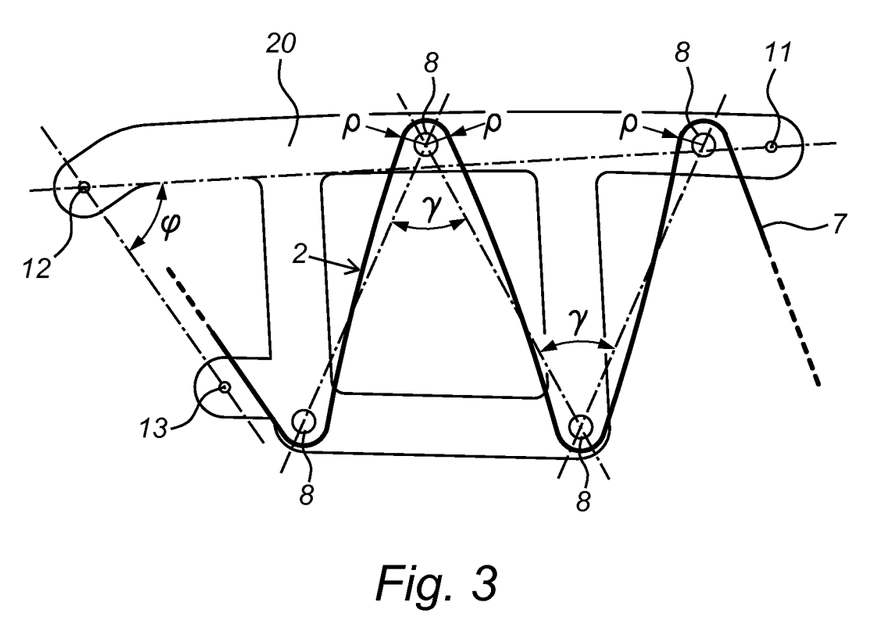
FIG. 3: a side view of a spacer of the holding system according to the present invention.

FIG. 3 shows a side view of the spacer 20 of the present invention. The guiding elements 8 are shown, as well as the first end 12 and the second end 11. The first end 12 may be divided into two first ends, i.e. first end 12 and first end 13. Preferable both first ends 12, 13 are provided with retaining elements (not shown) to hold the control body (not shown) of a medical instrument 2 at a predefined angle φ. By defining angle φ, the operator (not shown) is able to easily access the holder (not shown) in case the spacer 20 is in its downward position, whereas the medical instrument 2 is positioned as optimal as possible in the closable space (not shown) in case the spacer 20 is in its upward position, e.g. providing the most optimal position of a control body of an endoscope when placed in the closable drying space of a drying cabinet.

FIG. 3 further shows the flexible part 7 of a medical instrument 2 guided along the guiding elements 8. The guiding elements 8 are positioned such that the bending radii ρ of the flexible part 7 of the medical instrument 2 do not exceed a predefined minimum. Typically, the bending radii of the flexible part 7 may not exceed a minimum of 40 millimetre. In order to facilitate this, the guiding elements 8 are positioned on the spacer 20 in a staggered pattern wherein the angle γ of the vertices is about 55°.

Figure 4:
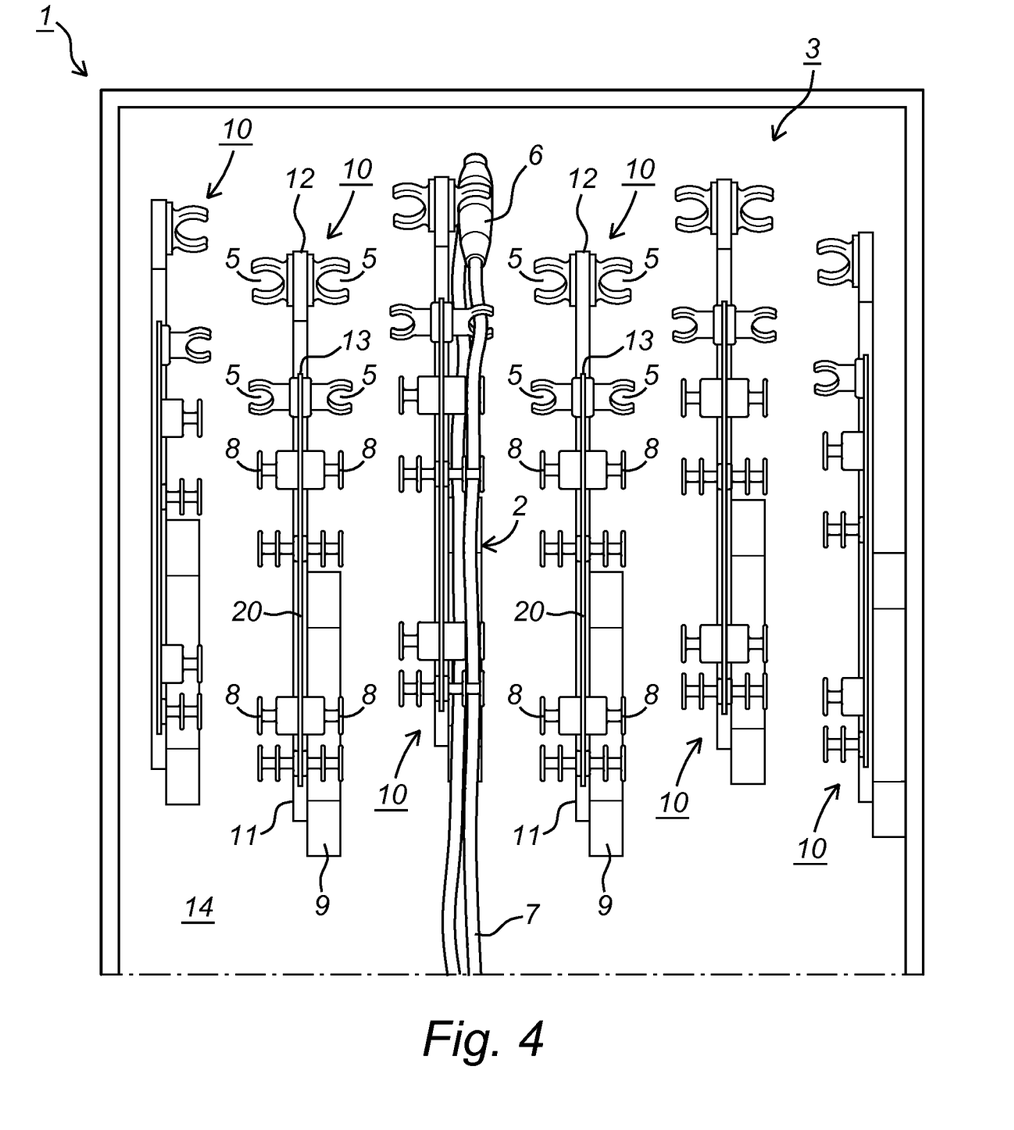
FIG. 4: a front view of the device according to the present invention.

FIG. 4 shows a front view of the closable space 3 of the device 1 according to the present invention. Holding systems 10 comprising a spacer 20, guiding elements 8, retaining elements 5, first ends 12, 13, second end 11 and hinge system 9 are shown, wherein the holding systems 10, i.e. hinge systems 9, are arranged in wavy pattern. By providing the wavy pattern, the control body 6 of the medical instrument 2 does not interfere with an adjacent control body of another medical instrument (not shown).

Figure 5:
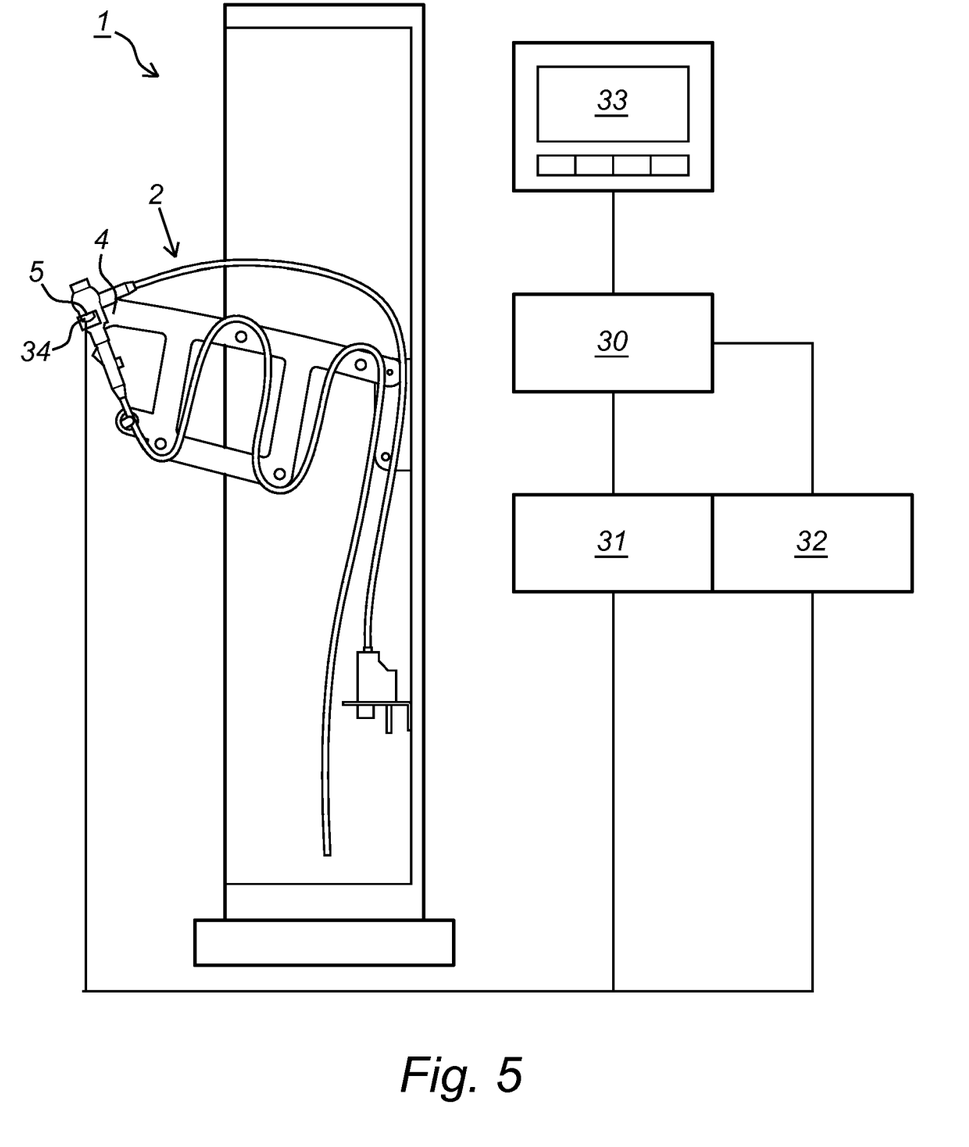
FIG. 5: a schematic representation of the identification system according to the present invention.

FIG. 5 shows a schematic representation of the device 1 comprising the identification system 31 according to the present invention. The identification system 31 is connected to a control system 30. The identification system 31 is further connected to identification means 34 connected to the retaining elements 5 of the holder 4. The control system 30 may further be connected to status indication system 32 connected to the identification means 34 as well to indicate the status of the medical instrument 2 connected to the retaining elements 5 of holder 4. The device 1 may further be provided with an information device 33 connected to the control system 30. The information device 33 may be configured to present information about the status of the various medical instruments 2 suspended in the device 1 and/or to receive any input from the operator of, for example, the medical instrument 2 to be suspended.

The invention claimed is:

1. A holding system for suspending one or more medical instruments in a closable space adapted therefore, such as a drying cabinet for endoscopes, comprising:
    a holder for holding at least one medical instrument; and
    at least one retaining element connected to the holder for retaining the at least one medical instrument to the holder,
the holding system further comprises a spacer, wherein:
    a first end of the spacer is connected to the holder; and
    a second end of the spacer is provided with a hinge system for hingedly connecting the spacer to a wall of the closable space,
wherein the at least one retaining element is configured to clampingly receiving the at least one medical instrument to be suspended,
    wherein the medical instrument to be suspended comprises a control body and wherein the at least one retaining element is configured to retain the control body to the holder,
    wherein the at least one retaining element comprises a ring-shaped passage opening for receiving the control body of the medical instrument to be suspended,
    wherein the peripheral wall of the ring-shaped passage opening is provided with an opening for receiving another part of the medical instrument connected to the control body, such as the flexible part of an endoscope,
    wherein the hinge system is configured to damp a downward movement of the holder in a direction facing away from the wall,
    wherein the hinge system is configured to automatically move the holder from a predefined position of the holder in an upward direction toward the wall,
    wherein the holder is provided with two or more retaining element for receiving not more than two medical instruments,
    wherein the spacer is provided with one or more guiding elements for guiding the suspending part of a medical instrument received by the holder along the guiding elements.

2. The holding system according to claim 1, wherein the guiding elements are positioned on the spacer according to a zigzag-pattern.

3. The holding system according to claim 2, wherein the guiding elements are positioned such that the bending radius of the flexible suspended part of the medical instrument received by the holder is not smaller than 8 centimeters.

4. The holding system according to claim 3, wherein the guiding elements are positioned such that a zigzag-pattern is formed by the guiding elements wherein the angle of the vertices is within the range of 45° to 65°.

5. The holding system according to claim 4, wherein the distance between the first end and the second end of the spacer is within the range of 50 centimeters to 90 centimeters.

6. The holding system according to claim 5, wherein the at least one retaining element is configured such that the angle between the spacer and the control body of a medical instrument to be suspended received by the at least one retaining element is within the range of 30° to 80°.

7. A device for suspending one or more medical instruments, such as a drying cabinet for endoscopes, comprising:
a closable space for receiving the one or more medical instruments to be suspended;
a plurality of holders positioned in the closable space, wherein each of the holders is configured to hold the one or more medical instruments, and wherein each of the holders is provided with at least one retaining element for holding the one or more medical instruments to be suspended; and
a control system comprising an identification system configured for identifying the holders,
wherein the at least one retaining element of each holder is provided with at least one identification means connected to the identification system, wherein the identification means is configured to identify the retaining element of the respective holder,
wherein the medical instrument to be suspended comprises a control body and wherein the at least one retaining element is configured to retain the control body to the holder,
wherein the at least one retaining element comprises a bracket,
wherein the bracket is configured to clampingly or releasably receiving at least one of the one or more medical instruments to be suspended,
wherein the at least one retaining element comprises a ring-shaped passage opening for receiving the control body of the medical instrument to be suspended,
wherein the peripheral wall of the ring-shaped passage opening is provided with an opening for receiving another part of the medical instrument connected to the control body, such as the flexible part of an endoscope,
wherein the at least one identification means comprises a visual identification means for identifying by means of visual indication the retaining element of the respective holder
wherein the at least one identification means comprises a light source, such as one or more LED lamps,
further wherein the light source is arranged on or in the holder and positioned such that the light source illuminates the retaining element,
further wherein the light source is arranged on the position the retaining element is connected to the respective holder,
further wherein the retaining element illuminated by the light source is made from light-guiding material,
further wherein the light-guiding material is an illuminating material,
further wherein the illuminating material comprises a semi-transparent plastic, such as polypropylene,
further wherein the holders are displaceable relative to each other,
further wherein the at least one identification means is positioned such that by displacement of the holder and the position of the identification means relative to the retaining element is unchanged,
further wherein the device comprises a drying cabinet and wherein the medical instrument to be suspended comprises an endoscope
further wherein the closable space comprises a drying space
further wherein the control system comprises a status indication system for displaying the status of a medical instrument connected with a holder,
further wherein the status indication system is connected to the at least one identification means for displaying the status of the medical instrument connected with the respective holder
further wherein the device is used for suspending one or more medical instruments,
further wherein the device comprises a drying cabinet and medical instrument comprises an endoscope, wherein each of the plurality of holders positioned in the space comprises a holding system, wherein the holding system comprises
a holder for holding at least one medical instrument; and
at least one retaining element connected to the holder for retaining at least one medical instrument to the holder,
the holding system further comprises a spacer, wherein:
a first end of the spacer is connected to the holder; and
a second end of the spacer is provided with a hinge system for hingedly connecting the spacer to a wall of the closable space,
wherein the at least one retaining element is configured to clampingly receiving the at least one medical instrument to be suspended
further wherein the second end of the spacer is hingedly connected to the wall of the closable space,
further wherein the second end of the spacer is connected to the wall of the closable space at a height within the range of 90 to 170 centimeters,
further wherein the hinge system is configured such that the angle between the spacer and the wall of the closable space does not exceed 90°,
further wherein the hinged system is configured such that the angle between the spacer and the wall of the closable space is at least 0°,
further wherein the at least one retaining element of each of the holder is configured such that the angle between the wall of the closable space and a control body of a medical instrument suspended in the closable space received by the at least one retaining element is within the range of 40° to 70° and
wherein the hinge systems of the plurality of holder positioned in the closable space are connected to the wall according to a wavy pattern.

8. A device for suspending one or more medical instruments, such as a drying cabinet for endoscopes, comprising:
a closable space for receiving the one or more medical instruments to be suspended;
a plurality of holders positioned in the closable space, wherein each of the holders is configured to hold the one or more medical instruments, and wherein each of the holders is provided with at least one retaining element for holding the one or more medical instruments to be suspended; and
a control system comprising an identification system configured for identifying the holders,
wherein the at least one retaining element of each holder is provided with at least one identification means connected to the identification system, wherein the identification means is configured to identify the retaining element of the respective holder, wherein the medical instrument to be suspended comprises a control body and wherein the at least one retaining element is configured to retain the control body to the holder, wherein the at least one retaining element comprises a bracket, wherein the bracket is configured to clampingly or releasably receiving at least one of the one or more medical instruments to be suspended, wherein the at least one retaining element comprises a ring-shaped passage opening for receiving the control body of the medical instrument to be suspended, wherein the peripheral wall of the ring-shaped passage opening is provided with an opening for receiving another part of the medical instrument connected to the control body, such as the flexible part of an endoscope, wherein the at least one identification means comprises a visual identification means for identifying by means of visual indication the retaining element of the respective holder wherein the at least one identification means comprises a light source, such as one or more LED lamps, further wherein the light source is arranged on or in the holder and positioned such that the light source illuminates the retaining element, further wherein the light source is arranged on the position the retaining element is connected to the respective holder, further wherein the retaining element illuminated by the light source is made from light-guiding material, further wherein the light-guiding material is an illuminating material, and further wherein the illuminating material comprises a semi-transparent plastic, such as polypropylene.

9. The device according to claim 8, wherein the holders are displaceable relative to each other, wherein the at least one identification means is positioned such that by displacement of the holder, the position of the identification means relative to the retaining element is unchanged.

10. The device according to claim 8, wherein the device comprises a drying cabinet and wherein the medical instrument to be suspended comprises an endoscope.

11. The device according to claim 8, wherein the closable space comprises a drying space.

12. The device according to claim 8, wherein the control system further comprises a status indication system for displaying the status of a medical instrument connected with a holder.

13. The device according to claim 12, wherein the status indication system is connected to the at least one identification means for displaying the status of the medical instrument connected with the respective holder.

14. The device according to claim 8, wherein the device comprises a drying cabinet and the medical instrument comprises an endoscope, wherein each of the plurality of holders positioned in the space comprises a holding system, wherein the holding system comprises a holder for holding at least one medical instrument; and at least one retaining element connected to the holder for retaining at least one medical instrument to the holder, wherein the holding system further comprises a spacer, wherein: a first end of the spacer is connected to the holder; and a second end of the spacer is provided with a hinge system for hingedly connecting the spacer to a wall of the closable space.

15. The device according to claim 14, wherein the second end of the spacer is hingedly connected to the wall of the closable space.

16. The device according to claim 14, wherein the second end of the spacer is connected to the wall of the closable space at a height of [90, 170] centimeters, at a height of [110, 150] centimeters or at a height of about 125 centimeters.

17. The device according to claim 14, wherein the hinge system is configured such that the angle between the spacer and the wall of the closable space does not exceed 90°, does not exceed 85°, or does not exceed 80°.

18. The device according to claim 14, wherein the hinged system is configured such that the angle between the spacer and the wall of the closable space is at least 0°, at least 4°, or at least 8°.

19. The device according to claim 14, wherein the at least one retaining element of each holder is configured such that the angle between the wall of the closable space and a control body of a medical instrument suspended in the closable space received by the at least one retaining element is [40, 70]°, [50, 60]°, or about 55°.

20. The device according to claim 14, wherein the hinge systems of the plurality of holders positioned in the closable space are connected to the wall according to a wavy pattern.

* * * * *